United States Patent [19]

Bennett

[11] Patent Number: Plant 5,523

[45] Date of Patent: Jul. 30, 1985

[54] MINIATURE ROSE PLANT NAMED BLOOMER GIRL

[76] Inventor: Cecilia L. D. Bennett, 489 Minot Ave., Chula Vista, Calif. 92010

[21] Appl. No.: 563,297

[22] Filed: Dec. 19, 1983

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant, named 'Bloomer Girl', which is characterized by its abundance of coral pink blooms and vigorous plant growth.

1 Drawing Figure

The present invention relates to a new and distinct variety of a hardy, dwarf, bush plant of the miniature class; the variety being primarily characterized as a pink blend.

The variety is further characterized by:

Long stemmed blooms, borne singly or in sprays of 3 to 5 or more, held very erect and well above the foliage.

Has a slight fragrance.

The plant ranges in height from 15 to 24 inches. The canes are sturdy and erect, heavily branched with medium to heavy foliage covering. The plant is a prolific bloomer that does well either in the green house or outdoors.

The plant has good growth habits, well shaped and attractive in appearance, bearing numerous leaflets of average size.

The seed parent was Futura (U.S. Plant Pat. No. 3,569), and the pollen parent was Pink Petticoat (Miniature Rose Plant, pink blend; Leslie E. Strawn; introduced by Pixie Treasures, 1979).

Subsequent to the origination of the variety, I have successfully reproduced it at Tiny Petals Nursery located at aforesaid retaining the distinguishing characteristics through succeeding propagations by cuttings.

The descriptive matter which follows pertains to roses grown and color values observed in plants and newly opened blooms in the months of August and September. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant named 'Bloomer Girl', the following is a detailed description/thereof in outline; all major color plate identifications being by reference to The British Color Council Horticultural Colour Chart, except where common terms of color definition are employed.

Type: Hardy, dwarf, bushy, green house or outdoor, garden decorative potted plant.

Class: Miniature.

Variety name: Bloomer Girl.

Flowers borne: Usually one to a stem or in sprays of 3 to 5 or more on erect stems with foliage well below the blooms.

Quanity of blooms: Heavy both outdoors or green house grown.

Bud:

*Peduncle.*—Variable (20 to 40 mm); average to large diameter and sturdy; near Pod Green (061 to 061/2 page 120) with little or no tinting of bronze.

*Hairs.*—Extremely small and numerous; located over entire surface of peduncle, calyx tube and sepals.

*Calyx.*—Color is near Pod Green (061 to 061/2 page 120).

*Opening.*—Opens well in all weather.

Bloom:

*Size when fully open.*—Average for a miniature variety (35 to 40 mm).

*Petalage.*—Double — Averaging 30 to 35 petals, arranged regularly, plus petaloids (10 to 15 or more).

*Form.*—Urn-shaped to ovoid as the bloom progresses. The fully opened bloom has a very circular appearance when viewed from the top, with the outermost petals quilled and drawn under and the other petals arched gently downward but with no sign of quilling.

Petals: Fairly thick with good substance; matte finish on both the upper and under surfaces.

*Shape.*—Obovate form with a slight peak at the apex. The outermost petals are slightly boarder obovate than the rest of the petals.

Color: Newly opened flowers from plants grown outdoors (August and September 1983), Chula Vista, Calif.:

*Outside petals.*—Upper Surface — Ranging from near Vermillion (18/2 to 18/3 page 18) to near Begonia (619 to 619/2 page 146) with a small area of white at the base and a tip of Naples Yellow (403/2 page 121).

*Under surface.*—Ranging from near Vermillion (18/2 to 18/3 page 18) to near Begonia (619/1 to 619/3 page 146) with a small area at the base of white blending to a tip of Naples Yellow (403/3 page 121).

*Intermediate and inner petals.*—Same as the outside petals.

*Flower longevity.*—(September 1983) Plant in pot 3 to 5 days from bud with sepals spreading to fully opened bloom. Holding at fully open with gradual fading of the color for an additional 3 or 4 days before the bloom begins to drop petals. Cut blooms at livingroom temperature, the bloom may last 3 to 5 days or longer from bud with sepals spreading to fully open.

Reproductive organs:

*Stamens.*—Generous amount arranged uniformly around the pistil.

*Filament.*—Average to long in length.

*Pollen.*—Abundant.

*Pistil.*—Long, abundant and compact.

*Styles.*—Long; ranging in color from pale green at the base to red with a cap of pale yellow.

*Ovaries.*—All encased in the calyx.

*Hips.*—Produced better than 50% of the time as the bloom passes; Color — Near Pod Green (061 to 061/2 page 120) with occasional tinting of bronze as the hip matures.

*Seeds.*—Usually 2 to 5 large seeds produced in each mature hip.

*Sepals.*—Permanent; lanceolate-shaped; open as the bloom opens, but does not usually recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Near Spinach Green (0960 to 0960/3 page 187) with slight to heavy tinting of bronze on the newer foliage. The upper surfaces have a semi-glossy finish, and the under surfaces have a matte finish of a slightly lighter shade than the upper surfaces.

*Rachis.*—Medium strength; upper surface is grooved with very small hairs over the length of it. Under surface also contains many small hairs and some small hooked thorns as well.

*Stipules.*—Varying in length from short to medium; average width; tapering auricles angled outward at about 45 degrees.

Growth:

*Habit.*—Dwarf, bushy, much branched; average to large height for a miniature rose plant.

*Growth.*—Vigorous.

*Canes.*—Medium; sturdy; held very erect.

*Main stems.*—Color — Ranging from near Lettuce Green (861 to 861/3 page 176) to near Scheeles Green (860/3 to 860/1 page 175) with little or no bronzing.

*Thorns.*—Averaging less than 3 per 10 cm on the main stems to less than 12 per 10 cm on the branches with small prickles or hairs. Pale yellow in color with occasional bronzing; average size for a miniature rose plant; slender; may be straight (most typical on the main stems and branches or slightly hooked downward (most typical on the underside of the rachis).

*Branches.*—Color — Same as main stems.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant named 'Bloomer Girl' of hardy, dwarf, bushy, much branched habit, substantially as illustrated and described, characterized by its abundance of coral pink blooms, usually borne singly or in sprays of 3 to 5 or more, and its vigorous growth habit. The plant may be propagated from cuttings, and it grows well outdoors or in the green house.

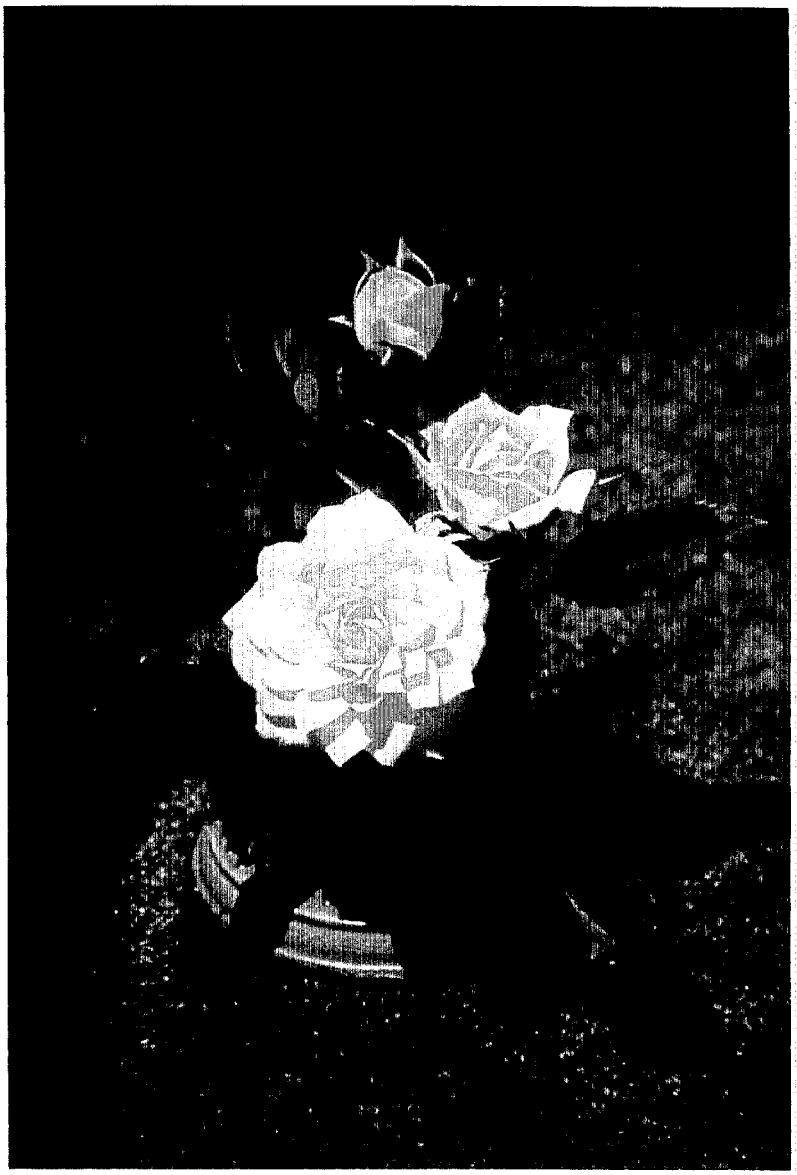

* * * * *